US008041047B2

(12) United States Patent
Matsumoto et al.

(10) Patent No.: US 8,041,047 B2
(45) Date of Patent: Oct. 18, 2011

(54) PLUG, SOUND INPUTTING AND OUTPUTTING APPARATUS, AND NOISE CANCEL SYSTEM

(75) Inventors: Ryota Matsumoto, Tokyo (JP); Ichiro Nakajima, Chiba (JP); Osamu Koshida, Saitama (JP); Shinya Yudate, Ehime (JP)

(73) Assignee: Sony Corporation, Tokyo (JP)

( * ) Notice: Subject to any disclaimer, the term of this patent is extended or adjusted under 35 U.S.C. 154(b) by 1069 days.

(21) Appl. No.: 11/899,094

(22) Filed: Sep. 4, 2007

(65) Prior Publication Data

US 2008/0226091 A1 Sep. 18, 2008

(30) Foreign Application Priority Data

Sep. 8, 2006 (JP) ................................. 2006-243903

(51) Int. Cl.
*A61F 11/06* (2006.01)
*G10K 11/16* (2006.01)
*H03B 29/00* (2006.01)

(52) U.S. Cl. .......... 381/71.1; 381/74; 381/384; 439/669

(58) Field of Classification Search ................. 381/71.1, 381/74, 384; 439/669
See application file for complete search history.

(56) References Cited

U.S. PATENT DOCUMENTS

| | | | | |
|---|---|---|---|---|
| 6,394,852 | B1 | 5/2002 | Huang | |
| 6,439,933 | B1 | 8/2002 | Moji | |
| 6,461,199 | B1 | 10/2002 | Koga et al. | |
| 6,616,487 | B1 | 9/2003 | Lai | |
| 6,672,906 | B1 * | 1/2004 | Kimura | 439/668 |
| 6,964,586 | B2 | 11/2005 | Siddiqui | |
| 2007/0160223 | A1 * | 7/2007 | Cusack, Jr. | 381/71.1 |
| 2008/0090465 | A1 | 4/2008 | Matsumoto et al. | |

FOREIGN PATENT DOCUMENTS

| | | | |
|---|---|---|---|
| EP | 1202400 | A | 5/2002 |
| EP | 1511128 | A | 3/2005 |
| JP | 09-204966 | | 8/1997 |
| WO | WO 02/052684 | A | 7/2002 |

* cited by examiner

*Primary Examiner* — Phat Cao
(74) *Attorney, Agent, or Firm* — Wolf, Greenfield & Sacks, P.C.

(57) ABSTRACT

Herein disclosed a sound inputting and outputting apparatus for being connected to an external apparatus which includes a noise cancel signal production section, a storage section and a reproduction section, including: a first auricle mounting section; a second auricle mounting section; and a plug.

30 Claims, 17 Drawing Sheets

PLUG, SOUND INPUTTING AND OUTPUTTING APPARATUS, AND NOISE CANCEL SYSTEM

CROSS REFERENCES TO RELATED APPLICATIONS

The present invention contains subject matter related to Japanese Patent Application JP 2006-243903 filed in the Japan Patent Office on Sept. 8, 2006, the entire contents of which being incorporated herein by reference.

BACKGROUND OF THE INVENTION

1. Field of the Invention

This invention relates to a plug, a sound inputting and outputting apparatus and a noise cancel system, and more particularly to a plug of a five-pole configuration and a sound inputting and outputting apparatus and a noise cancel system in which a plug of a five-pole configuration is used.

2. Description of the Related Art

A plug to be connected to a jack of various electronic equipments such as, for example, an acoustic equipment is provided at an end portion of, for example, an earphone, a headphone, or various connection cables.

Generally, such a plug as described above such as, for example, a plug provided on an earphone, a headphone or the like, has a three-pole configuration for a speaker L (left), a speaker R (right) and the ground as disclosed, for example, in Japanese Patent Laid-Open No. Hei 9-204966 (hereinafter referred to as Patent Document 1).

A sound inputting and outputting apparatus such as an earphone or a headphone in which such a plug as described above is provided includes a pair of auricle mounting portions for being mounted on a pair of auricles of a user. However, when sound is outputted from a pair of speakers of the sound inputting and outputting apparatus in a state wherein the auricle mounting portions are mounted on the auricles of the user, such a disadvantage sometimes occurs that external sound is inputted as noise to the auricles depending upon the external environment or the like.

Countermeasures for canceling such noise are available in the related art. According to one of the related art, a microphone and a circuit board on which a noise cancel circuit is formed are disposed in each of the auricle mounting portions of the sound inputting and outputting apparatus. The noise cancel circuit produces a noise cancel signal based on a noise signal inputted to the microphone, and the noise cancel signal is outputted from the speaker provided in each of the auricle mounting portions to cancel the noise.

SUMMARY OF THE INVENTION

However, according to the related art for canceling noise, not only a microphone but also a circuit board on which a noise cancel circuit is formed are disposed in each of the auricle mounting portions of the sound inputting and outputting apparatus. Therefore, the auricle mounting portions have a size increased as much, and this gives rise to a problem that the feeling of the user in mounting of the auricle mounting portions on the auricles is not good.

On the contrary, if it is tried to miniaturize the auricle mounting portions, then it becomes difficult to assure the space for arrangement of the circuit board, resulting in failure to achieve cancellation of noise.

Therefore, it is demanded to provide a plug, a sound inputting and outputting apparatus and a noise cancel system wherein a noise cancel function can be achieved.

According to the present invention, in order to achieve a noise cancel function, a plug of a five-pole configuration is used.

More particularly, according to an embodiment of the present invention, there is provided a plug for being inserted in a jack of an external apparatus which includes a noise cancel signal production section and a reproduction section to establish connection of first and second microphones and first and second speakers provided in a sound inputting and outputting apparatus to the external apparatus, including a first conductor configured to transmit a first noise signal to the external apparatus in response to first noise inputted to the first microphone, a second conductor configured to transmit a second noise signal to the external apparatus in response to second noise inputted to the second microphone, a third conductor configured to transmit a first synthesis signal of a first noise cancel signal produced by the noise cancel signal production section in response to the first noise signal and a first sound signal reproduced by the reproduction section to the first speaker, a fourth conductor for grounding, and a fifth conductor configured to transmit a second synthesis signal of a second noise cancel signal produced by the noise cancel signal production section in response to the second noise signal and a second sound signal reproduced by the reproduction section to the second speaker.

According to another embodiment of the present invention, there is provided a sound inputting and outputting apparatus for being connected to an external apparatus which includes a noise cancel signal production section for producing, in response to a noise signal inputted thereto, a noise cancel signal for reducing the noise signal, a storage section and a reproduction section for reproducing sound data stored in the storage section, including a first auricle mounting section including a first microphone and a first speaker, a second auricle mounting section including a second microphone and a second speaker, and a plug including a first conductor configured to output a first noise signal to the external apparatus in response to first noise inputted to the first microphone, a second conductor configured to output a second noise signal to the external apparatus in response to second noise inputted to the second microphone, a third conductor configured to transmit a first synthesis signal of a first noise cancel signal produced by the noise cancel signal production section in response to the first noise signal and a first sound signal reproduced by the reproduction section to the first speaker, a fourth conductor for grounding, and a fifth conductor configured to transmit a second synthesis signal of a second noise cancel signal produced by the noise cancel signal production section in response to the second noise signal and a second sound signal reproduced by the reproduction section to the second speaker, the plug being configured to be inserted into a jack provided on the external apparatus to establish connection thereof to the external apparatus.

According to a further embodiment of the present invention, there is provided a sound signal processing apparatus including a noise cancel signal production section configured to produce first and second noise cancel signals in response to first and second noise signals outputted from first and second microphones of a sound inputting and outputting apparatus in response to first noise and second nose inputted to the first and second microphones, respectively, a reproduction section configured to reproduce sound data stored in a storage section and output first and second sound signals, a synthesis section configured to synthesize the first and second noise cancel signals with the first and second sound signals to produce first and second synthesis signals, respectively, and a jack configured to be fitted with a plug of a five-pole configuration provided on the sound inputting and outputting apparatus and including a first conductor configured to transmit the first noise signal outputted from the first microphone, a second conductor configured to transmit the second noise signal outputted from the second microphone, a third conductor configured to transmit the first synthesis signal to the first speaker of the sound inputting and outputting apparatus, a fourth conductor for grounding, and a fifth conductor configured to transmit the second synthesis signal to the second speaker of the sound inputting and outputting apparatus.

According to a still further embodiment of the present invention, there is provided a noise cancel system including a sound signal processing apparatus, and a sound signal inputting and outputting apparatus, the sound signal processing apparatus including a noise cancel signal production section configured to produce a noise cancel signal in response to a noise signal inputted thereto, a reproduction section configured to reproduce a sound signal stored in a storage section, and a jack, the sound signal inputting and outputting apparatus including a first auricle mounting section including a first microphone and a first speaker, a second auricle mounting section including a second microphone and a second speaker, and a plug of a five-pole configuration including a first conductor configured to output a first noise signal to the sound signal processing apparatus in response to first noise inputted to the first microphone, a second conductor configured to output a second noise signal to the sound signal processing apparatus in response to second noise inputted to the second microphone, a third conductor configured to transmit a first synthesis signal of a first noise cancel signal produced by the noise cancel signal production section in response to the first noise signal and a first sound signal reproduced by the reproduction section to the first speaker, a fourth conductor for grounding, and a fifth conductor configured to transmit a second synthesis signal of a second noise cancel signal produced by the noise cancel signal production section in response to the second noise signal and a second sound signal reproduced by the reproduction section to the second speaker, the plug being configured to be inserted into a jack provided of the sound signal processing apparatus to establish connection between the sound inputting apparatus and the sound signal processing apparatus.

In the plug, sound inputting and outputting apparatus, sound signal processing apparatus and noise cancel system, first and second noise cancel signals are transmitted from the noise cancel signal production section provided in the external apparatus to the first and second speakers, respectively.

The above and other features and advantages of the present invention will become apparent from the following description and the appended claims, taken in conjunction with the accompanying drawings in which like parts or elements denoted by like reference symbols.

DETAILED DESCRIPTION OF THE PREFERRED EMBODIMENTS

Figure 1:
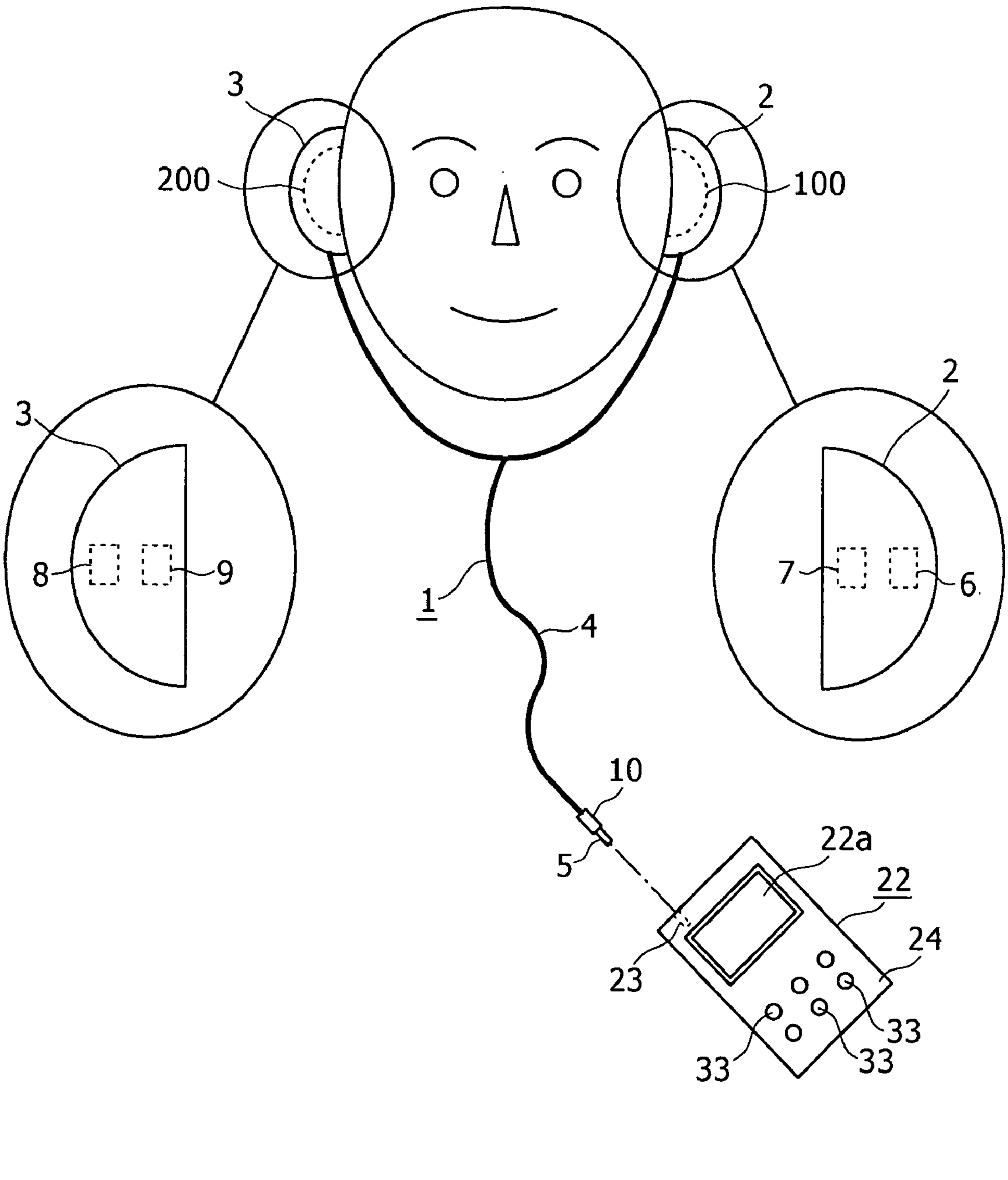
FIG. 1 is a schematic view showing a general configuration of a sound inputting and outputting apparatus to which the present invention is applied and an external apparatus.

Referring first to FIG. 1, there is shown a sound inputting and outputting apparatus 1 to which the present invention is applied. The sound inputting and outputting apparatus 1 may be, for example, an earphone or a headphone as seen in FIG. 1 and includes a pair of auricle mounting elements 2 and 3 for being mounted on the left and right auricles 100 and 200 of a user, respectively, and a plug 5 connected to the auricle mounting elements 2 and 3 through a connection cable 4.

The auricle mounting element 2 is mounted typically on the left side auricle 100 of the user. The auricle mounting element 2 has a first microphone 6 and a first speaker 7 built therein. The first microphone 6 is disposed typically on the outer side with respect to the first speaker 7 remote from the drum membrane of the user. In other words, the first microphone 6 is disposed remotely from the sound outputting side of the first speaker 7 with respect to the first speaker 7.

The auricle mounting element 3 is mounted typically on the right side auricle 200. The auricle mounting element 3 has a second microphone 8 and a second speaker 9 built therein. The second microphone 8 is disposed typically on the outer side with respect to the second speaker 9 remote from the drum membrane of the user. In other words, the second microphone 8 is disposed remotely from the sound outputting side of the second speaker 9 with respect to the second speaker 9.

The connection cable 4 includes five connection lines hereinafter described which are covered with an insulating material.

The plug 5 is partly covered with a cover 10 formed from a material having no electric conductivity such as, for example, a resin material.

Figure 2:
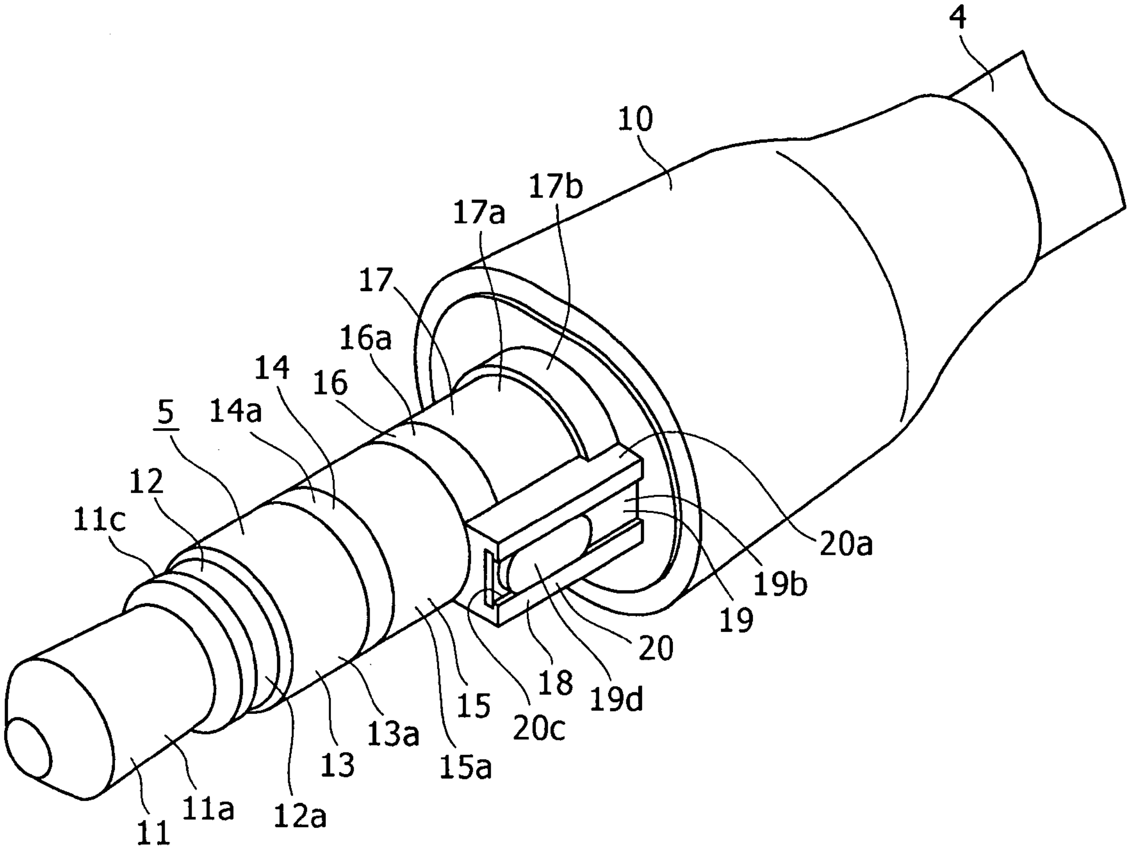
FIG. 2 is an enlarged perspective view showing a plug to which the present invention is applied.
Figure 3:
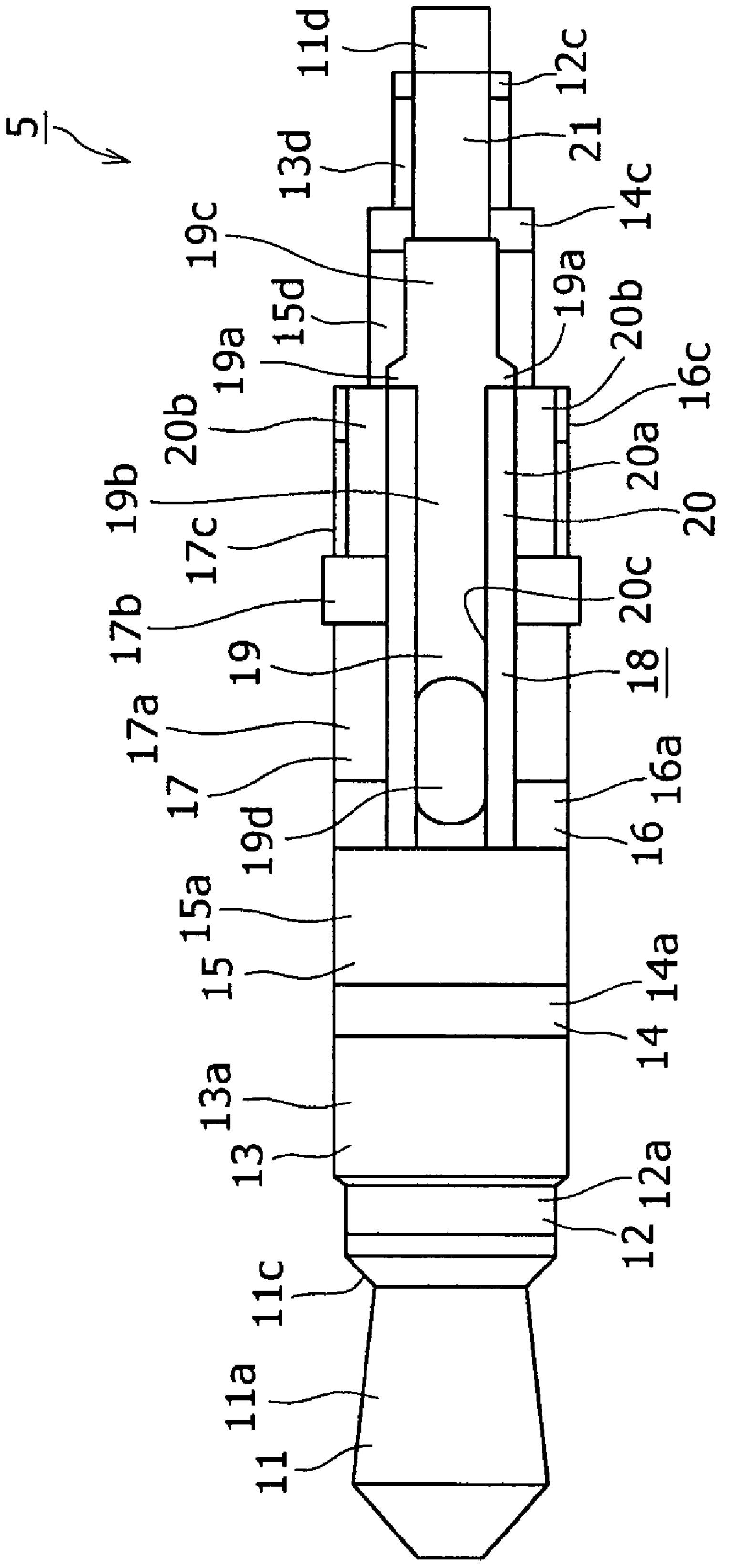
FIG. 3 is an enlarged side elevational view of the plug.
Figure 4:
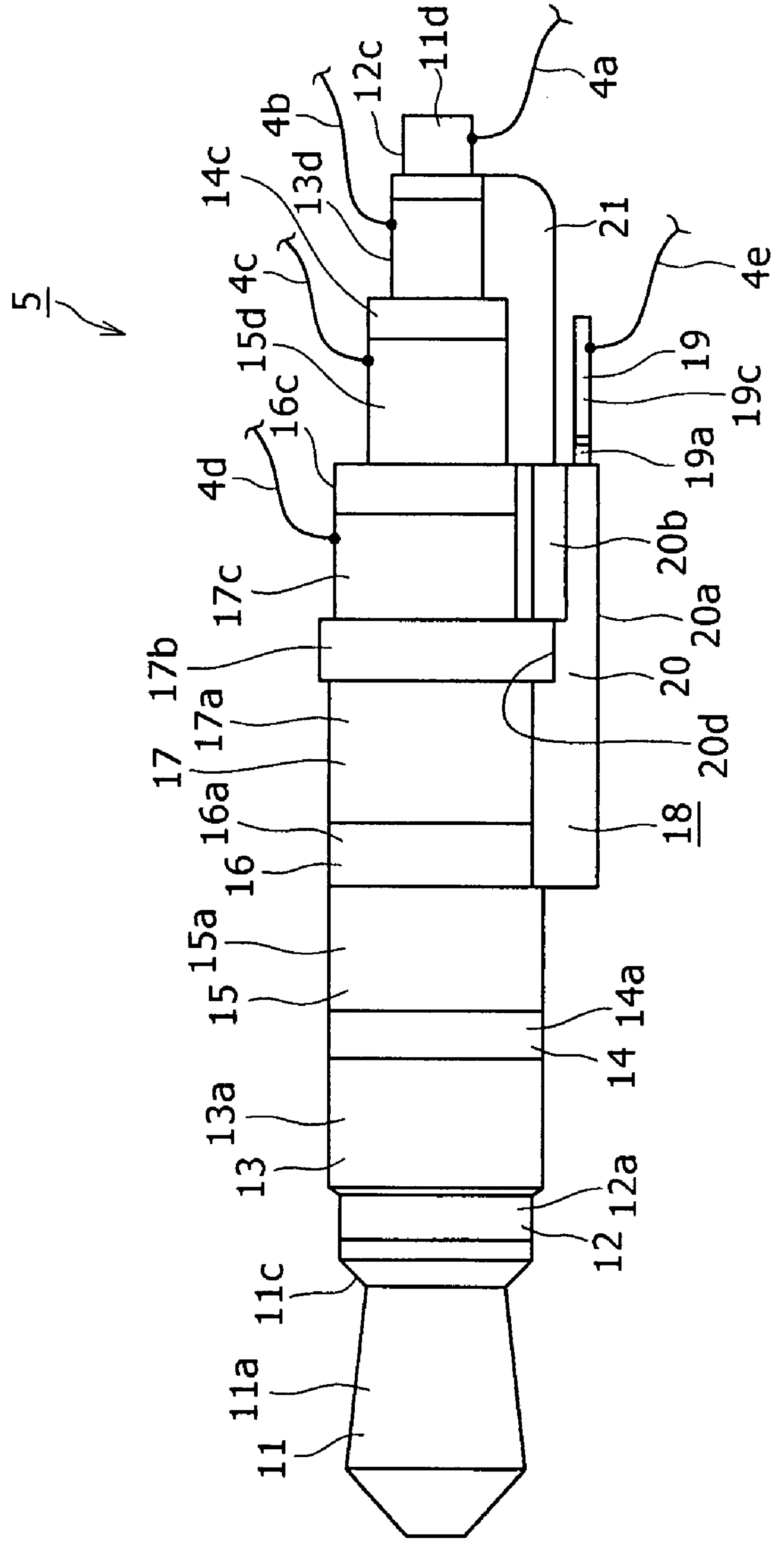
FIG. 4 is an enlarged side elevational view of the plug as viewed from a direction different from that in FIG. 3.

Referring now to FIGS. 2 to 4, the plug 5 includes a first conductor 11, a first insulator 12, a second conductor 13, a second insulator 14, a third conductor 15, a third insulator 16, a fourth conductor 17, a fourth insulator 18 and a fifth conductor 19. The first, second, third, fourth and fifth conductors 11, 13, 15, 17 and 19 are made of a metal material having high electrical conductivity. Meanwhile, the first, second, third and fourth insulators 12, 14, 16 and 18 are made of a material which does not have electrical conductivity such as a resin material or the like.

The first, second, third, fourth and fifth conductors 11, 13, 15, 17 and 19 are used, for example, as a terminal for the first speaker 7, a terminal for the second speaker 9, a terminal for the first microphone 6, a grounding terminal and a terminal for the second microphone 8, respectively.

It is to be noted that, while the first, second, third, fourth and fifth conductors 11, 13, 15, 17 and 19 are described as being used, for example, as a terminal for the first speaker 7, a terminal for the second speaker 9, a terminal for the first microphone 6, a grounding terminal and a terminal for the second microphone 8, respectively, it may be determined arbitrarily as what terminals the first, second, third, fourth and fifth conductors 11, 13, 15, 17 and 19 should individually be used.

The first conductor 11 is formed as a substantially round bar and has an electrode portion 11*a* of a large diameter and a fitting portion 11*b* of a small diameter. The first conductor 11 has a flange portion 11*c* provided between thereon the electrode portion 11*a* and the fitting portion 11*b* in such a manner as to be swollen outwardly. The first conductor 11 further has a cable connection portion 11*d* provided at an end portion of the fitting portion 11*b* thereof remote from the flange portion 11*c*.

The first conductor 11 further has an inclination face 11*e* formed on the outer periphery of the electrode portion 11*a* thereof such that it is inclined so as to displace to the center side of the round bar toward the fitting portion 11*b*. The length of the fitting portion 11*b* in the axial direction is greater than that of the electrode portion 11*a*. The diameter of the cable connection portion 11*d* is smaller than that of the electrode portion 11*a* but greater than that of the fitting portion 11*b*.

The first insulator 12 is formed in a substantially cylindrical shape and has a large diameter portion 12*a* provided at an end portion of the first insulator 12 in the axial direction and having an outer diameter greater than that of the other portion which is therefore formed as a small diameter portion 12*b*. The large diameter portion 12*a* is formed with a thickness greater than that of the small diameter portion 12*b*. A swollen portion 12*c* is formed at an end portion of the small diameter portion 12*b* remote from the large diameter portion 12*a* such that it is swollen a little outwardly in a radial direction of the round bar. Further, a shallow fitting concave portion 12*d* is formed on the outer face side of the first insulator 12 between the large diameter portion 12*a* and the swollen portion 12*c*.

The first insulator 12 is outwardly fitted with the fitting portion 1*b* of the first conductor 11. In this state wherein the first insulator 12 is outwardly fitted with the first conductor 11, the outer circumferential face of the large diameter portion 12*a* coincides with that of the flange portion 11*c*. The electrode portion 11*a*, flange portion 11*c* and cable connection portion 11*d* of the first conductor 11 are exposed to the outside.

The second conductor 13 is formed in a substantially cylindrical shape and has an electrode portion 13*a* of a large diameter and a fitting portion 13*b* of a small diameter. A substantially annular connection portion 13*c* is formed on the first conductor 13 such that it connects the electrode portion 13*a* and the fitting portion 13*b* to each other. Further, a cable connection portion 13*d* is provided at an end of the fitting portion 13*b* remote from the connection portion 13*c*.

The second conductor 13 is outwardly fitted with the first insulator 12. In the state wherein the second conductor 13 is outwardly fitted with the first insulator 12, the electrode portion 13*a* is connected to a portion of the large diameter portion 12*a* other than one end portion and the fitting portion 13*b* and the connection portion 13*c* are connected to the fitting concave portion 12*d* Further, the outer circumferential face of the fitting portion 13*b* coincides with that of the swollen portion 12*c*. Accordingly, part of the large diameter portion 12 and the swollen portion 12*c* of the second insulator 12 are exposed to the outside.

The second insulator 14 is formed in a substantially cylindrical shape and has a large diameter portion 14*a* provided at an end portion thereof in the axial direction and having a diameter greater than that of the other portion, which is provided as a small diameter portion 14*b*. The large diameter portion 14*a* is formed with a thickness greater than that of the small diameter portion 14*b*. A swollen portion 14*c* is provided at an end portion of the small diameter portion 14*b* remote from the large diameter portion 14*a* and is swollen outwardly a little. Further, a shallow fitting concave portion 14*d* is formed on the outer face side of the second insulator 14 between the large diameter portion 14*a* and the swollen portion 14*c*.

The second insulator 14 is outwardly fitted with the fitting portion 13*b* of the second conductor 13. In the state wherein the second insulator 14 is fitted with the second conductor 13, the outer circumferential face of the large diameter portion 14*a* coincides with that of the electrode portion 13*a* in a radial direction. The electrode portion 13*a* and the cable connection portion 13*d* of the second conductor 13 are exposed to the outside.

The third conductor 15 is formed in a substantially cylindrical shape and has a large diameter electrode portion 15*a* and a small diameter fitting portion 15*b*. A substantially annular connection portion 15*c* is provided on the first conductor 15 and connects the electrode portion 15*a* and the fitting portion 15*b* to each other. Further, a cable connection portion 15*d* is provided at an end portion of the fitting portion 15*b* remote from the connection portion 15*c*.

The third conductor 15 is outwardly fitted with the second insulator 14. In the state wherein the third conductor 15 is outwardly fitted with the second insulator 14, the third conductor 15 is connected to the fitting concave portion 14*d* and the outer circumferential face of the electrode portion 15*a* coincides with that of the large diameter portion 14*a* in a radial direction. Further, the outer circumferential face of the fitting portion 15*b* coincides with that of the swollen portion 14*c* in a radial direction. Accordingly, the large diameter portion 14*a* and the swollen portion 14*c* of the second insulator 14 are exposed to the outside.

The third insulator 16 is formed in a substantially cylindrical shape, and a large diameter portion 16*a* having a large outer diameter is provided one end portion of the third insulator 16 in the axial direction. A portion of the third insulator 16 contiguous to the large diameter portion 16*a* in the axial direction is formed as a small diameter portion 16*b*, and the other end portion of the third insulator 16 in the axis direction is formed as a swollen portion 16*c* having an outer diameter greater than that of the small diameter portion 16*b*. The large diameter portion 16*a* and the swollen portion 16*c* are formed with a thickness greater than that of the small diameter portion 16*b*. A shallow fitting concave portion 16*d* is formed on the outer face side of the third insulator 16 between the large diameter portion 16*a* and the swollen portion 16*c*.

The third insulator 16 is outwardly fitted with the fitting portion 15*b* of the third conductor 15. In the state wherein the third insulator 16 is outwardly fitted with the third conductor 15, the outer circumferential faces of the large diameter portion 16*a* and the swollen portion 16*c* coincide with the outer periphery of the electrode portion 15*a* in a radial direction. In the third conductor 15, the electrode 15*a* and the cable connection portion 15*d* are exposed.

The fourth conductor 17 is formed in a substantially cylindrical shape and has an electrode portion 17*a* and an annular projection 17*b* provided in an outwardly projecting manner on the outer circumferential face at a central portion of the electrode portion 17*a* in the axial direction. A cable connection portion 17*c* is provided at a portion of the electrode portion 17*a*.

The fourth conductor 17 is outwardly fitted with the fitting concave portion 16*d* of the third insulator 16. In the state wherein the fourth conductor 17 is outwardly fitted with the third insulator 16, the outer circumferential face of the electrode portion 17*a* coincides with those of the large diameter portion 16 and the swollen portion 16*c* in a radial direction. Accordingly, the large diameter portion 16*a* and the swollen portion 16*c* of the third insulator 16 are exposed to the outside.

Figure 6:
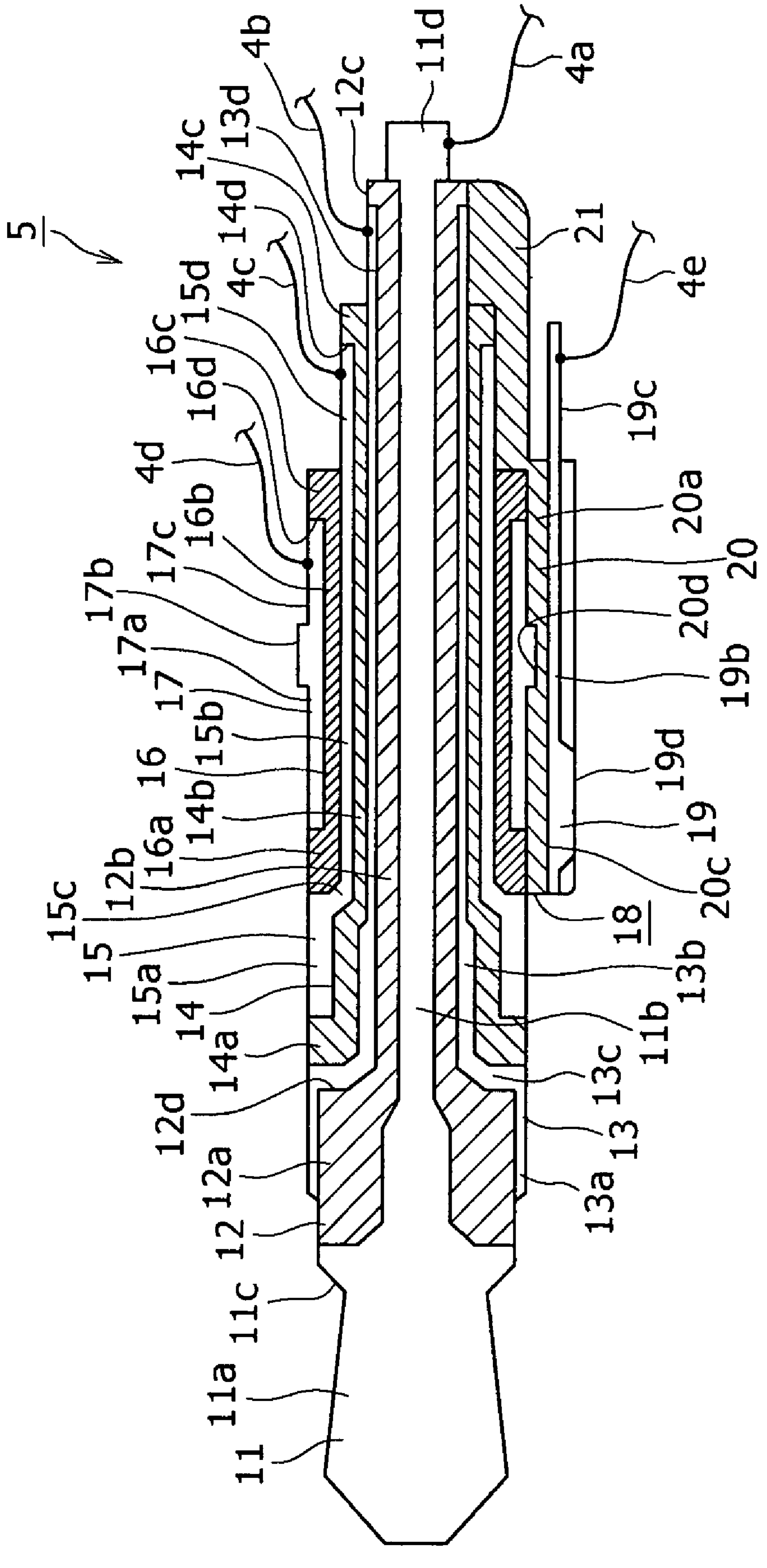
FIG. 6 is an enlarged sectional view of the plug taken a direction different from that in FIG. 5.
Figure 7:
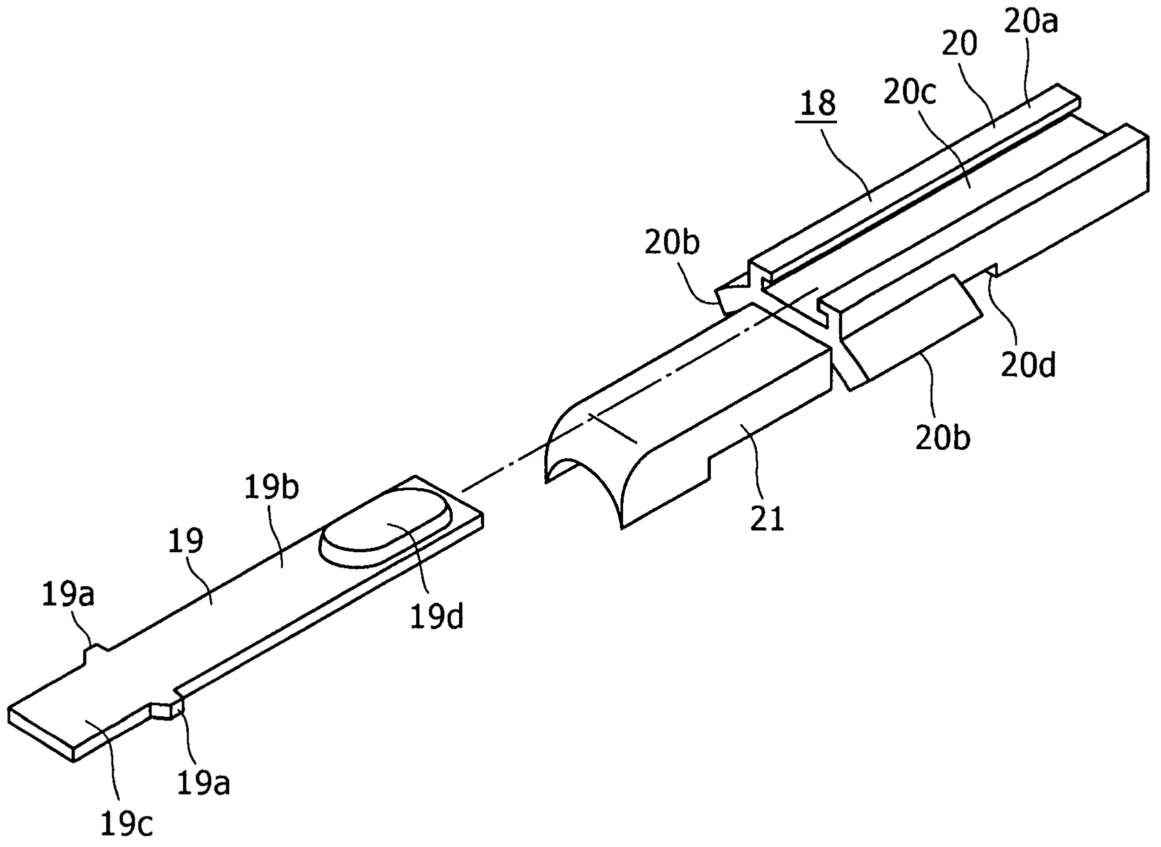
FIG. 7 is an enlarged perspective view showing a fourth insulator and a fifth conductor of the plug.

A conductor attachment portion 20 and an extension 21 are formed integrally on the outer periphery of the fourth insulator 18 as seen in FIGS. 4 and 6.

The conductor attachment portion 20 is formed long in one direction and has a main body portion 20*a* and a pair of projections 20*b* projecting in a lateral direction away from each other from an end portion of the main body portion 20*a* in a longitudinal direction. A conductor attachment groove 20*c* is formed on the main body portion 20*a* and extends in the longitudinal direction, and a fitting groove 20*d* is formed on the face of the conductor attachment portion 20 opposite to the face on which the conductor attachment groove 20*c* is formed and extends in the widthwise direction. The extension 21 is projected from an end face of the conductor attachment portion 20 in the longitudinal direction toward a direction perpendicular to the projection direction of the projections 20*b*.

The fourth insulator 18 is attached at the conductor attachment portion 20 thereof to part of the outer periphery of a portion of the third insulator 16 which extends from the large diameter portion 16*a* to the swollen portion 16*c*. Further, the fourth insulator 18 is attached at the extension 21 thereof to part of the outer periphery of a portion of the third conductor 15 which extends from the cable connection portion 15*d* to the swollen portion 12*c* of the first insulator 12. In the state wherein the fourth insulator 18 is attached in this manner, the fitting groove 20*d* is fitted with the projection 17*b* of the fourth conductor 17 and the conductor attachment portion 20 is positioned on the outer circumference side with respect to the extension 21.

The fifth conductor 19 is formed as a plate extending in one direction and has blocking projections 19*a* provided at an intermediate portion thereof in the longitudinal direction and projected away from each other. One side of the fifth conductor 19 with reference to the blocking projections l9*a* serves as an insertion portion 19*b* while the other side serves as a cable connection portion 19*c*. A connection projection 19*d* projected in a thicknesswise direction is provided at an end of the insertion portion 19*b* remote from the cable connection portion 19*c*.

The fifth conductor 19 is attached to the fourth insulator 18 by inserting the insertion portion 19*b* in the conductor attachment groove 20*c* as seen in FIG. 3. In the state wherein the fifth conductor 19 is attached to the fourth insulator 18, the blocking projections 19*a* thereof contact with one end face of the main body portion 20*a* and the cable connection portion 19*c* is positioned in a spaced relationship away from the extension 21 to the outer periphery side as seen in FIG. 4.

Figure 5:
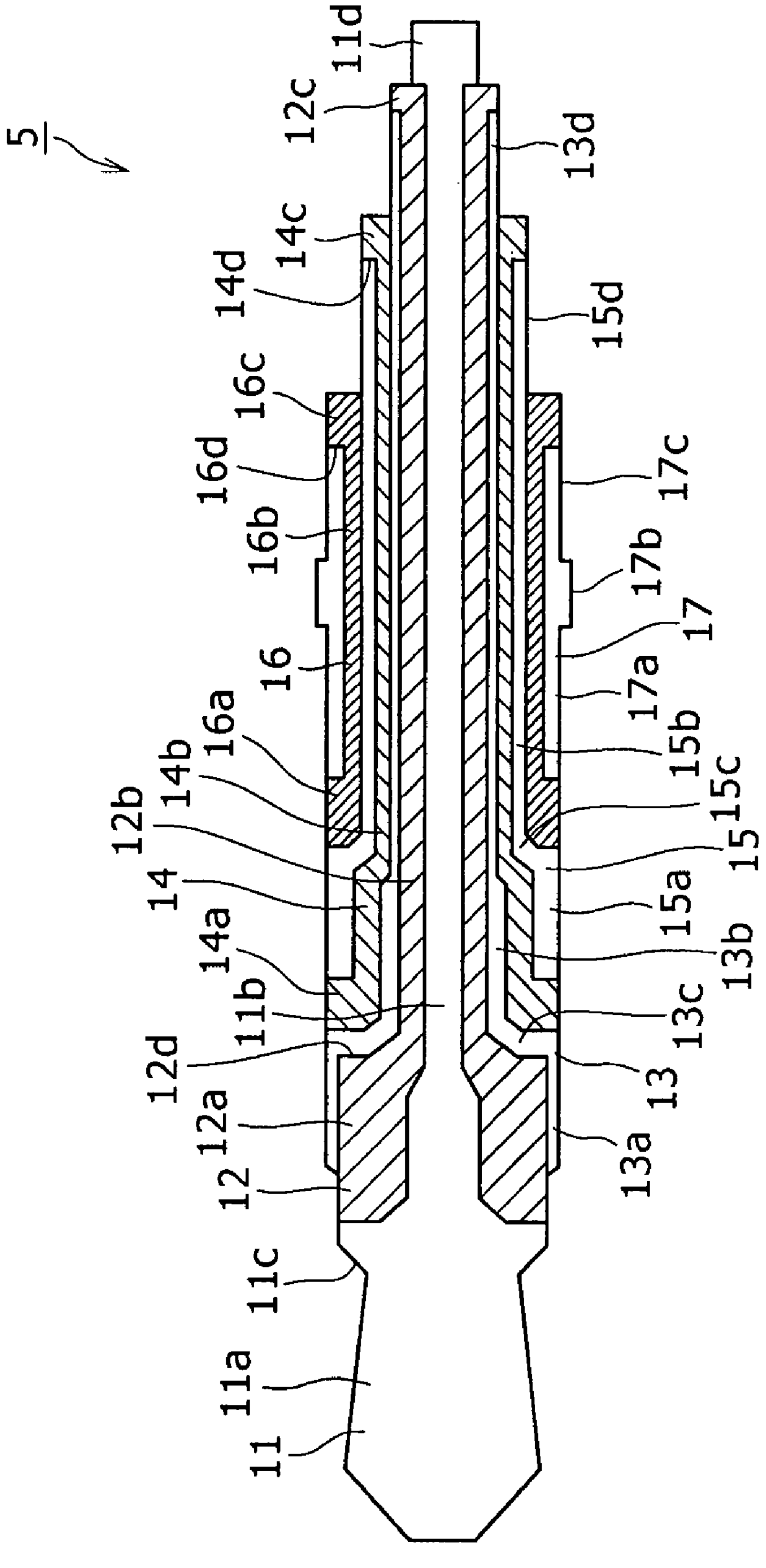
FIG. 5 is an enlarged sectional view of the plug.

Referring to FIGS. 5 and 6, in the plug 5 having the configuration described above, five connection lines 4*a*, 4*b*, 4*c*, 4*d* and 4*e* of the connection cable 4 are connected at one end portion thereof to the cable connection portions lid, 13*d*, 15*d*, 17*c* and 19*c* of the first, second, third, fourth and fifth conductors 11, 13, 15, 17 and 19, respectively, by means of, for example, soldering. The connection lines 4*a*, 4*b*, 4*c*, 4*d* and 4*e* are connected at the other end thereof, for example, to the first speaker 7, second speaker 9, first microphone 6, grounding terminal not shown and second microphone 8, respectively.

In the state wherein the connection lines 4*a*, 4*b*, 4*c*, 4*d* and 4*e* are connected to the respective portions of the plug 5, a portion of the fourth conductor 17 which extends from the projection 17*b* to the cable connection portion 11*d* of the first conductor 11 is covered with a cover 10 to close up and the cable connection portions 11*d*, 13*d*, 15*d*, 17*c* and 19*c* as seen in FIG. 2.

The plug 5 is connected to the jack 23 provided on the external equipment 22, which may be, for example, a music reproduction equipment, as seen in FIG. 1.

Figure 8:
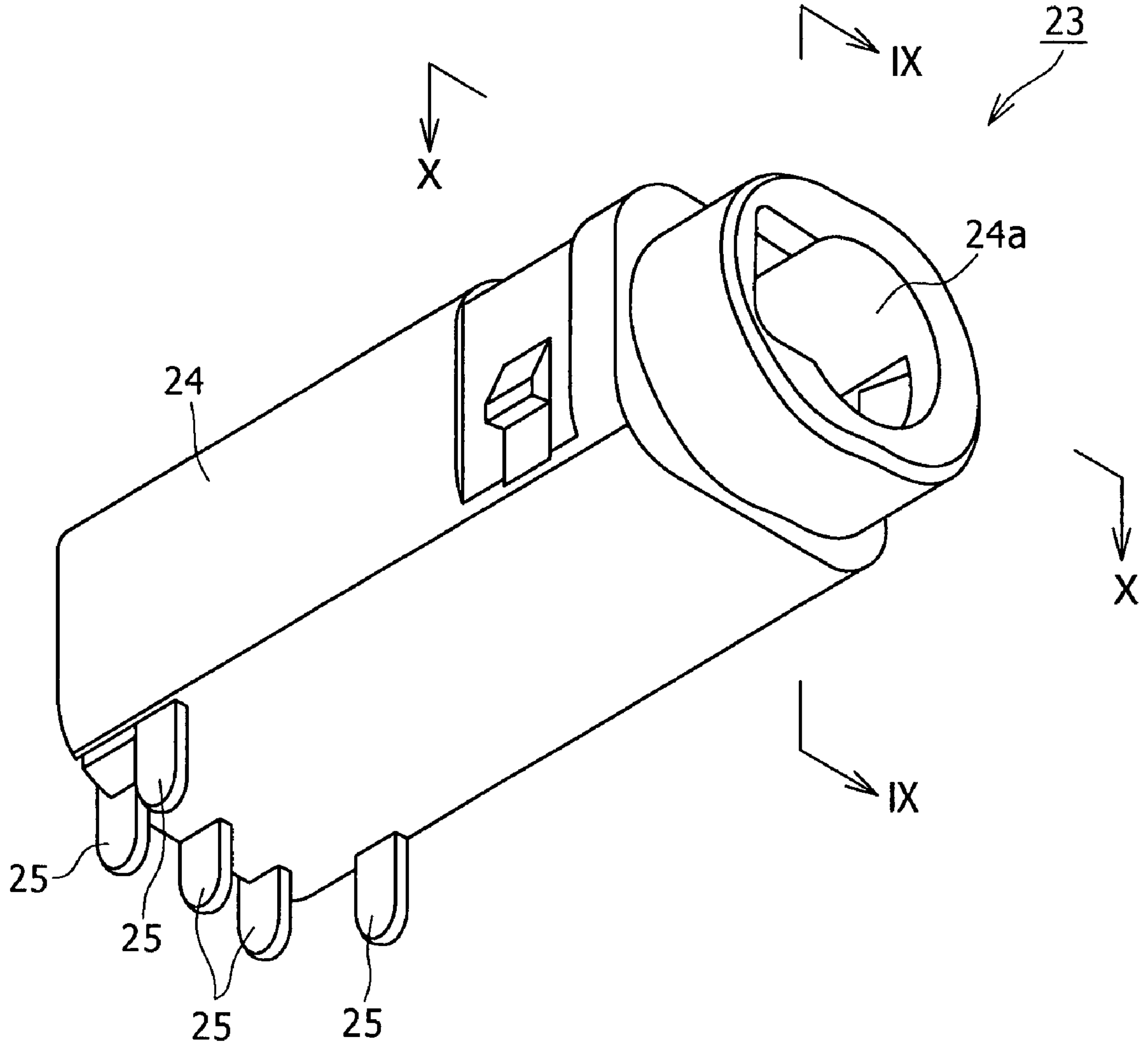
FIG. 8 is an enlarged perspective view of a jack of the external apparatus.

Referring to FIG. 8, the jack 23 includes a housing 24 on which several components are provided. A plug insertion hole 24*a* is formed on the housing 24 such that it is open in one direction. Five terminal pieces 25 are projected from an end portion of the jack 23 remote from the opening of the plug insertion hole 24*a*. The terminal pieces 25 are connected to a control circuit hereinafter described which is provided on the external equipment 22.

Figure 9:
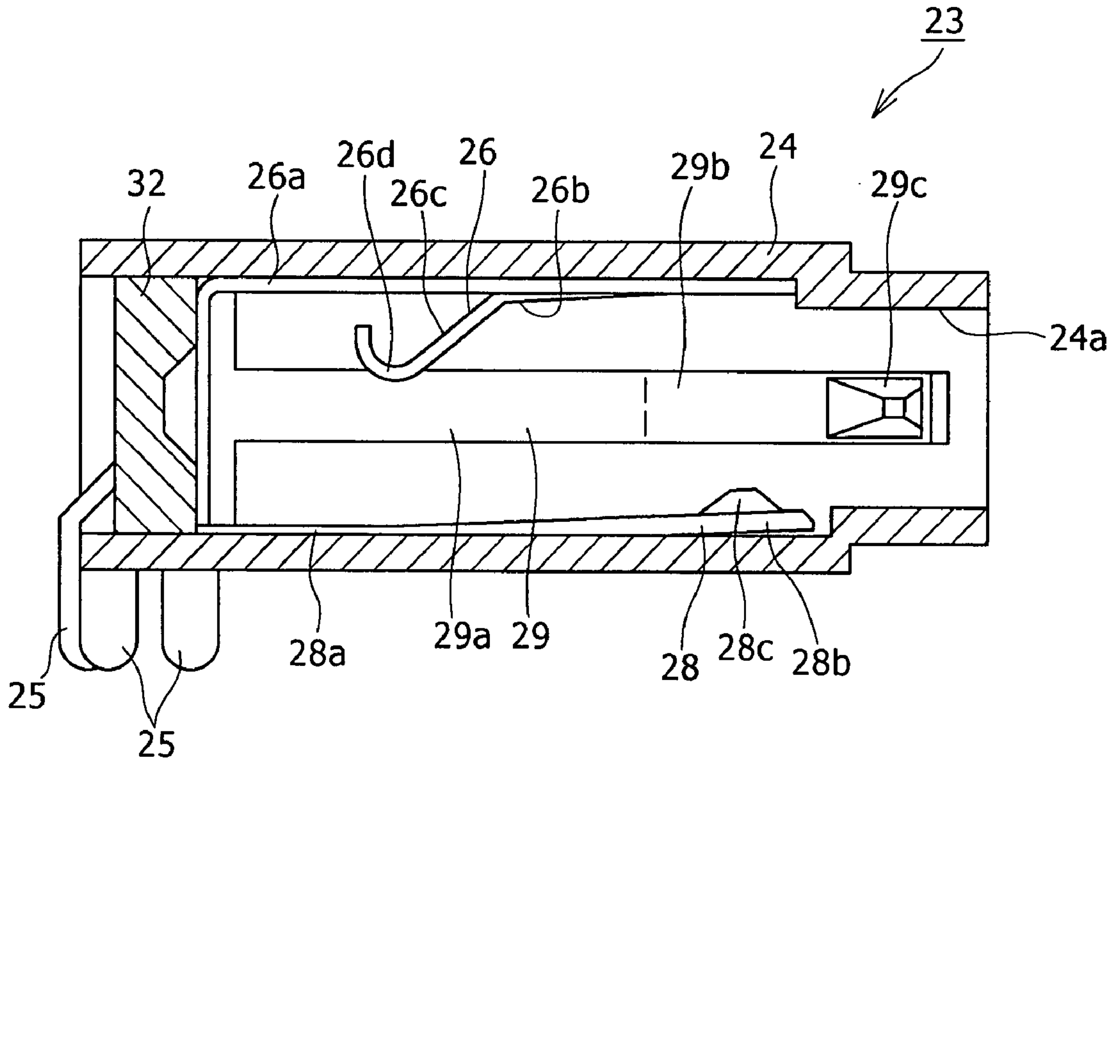
FIG. 9 is a sectional view taken along line IX-IX of FIG. 8.
Figure 10:
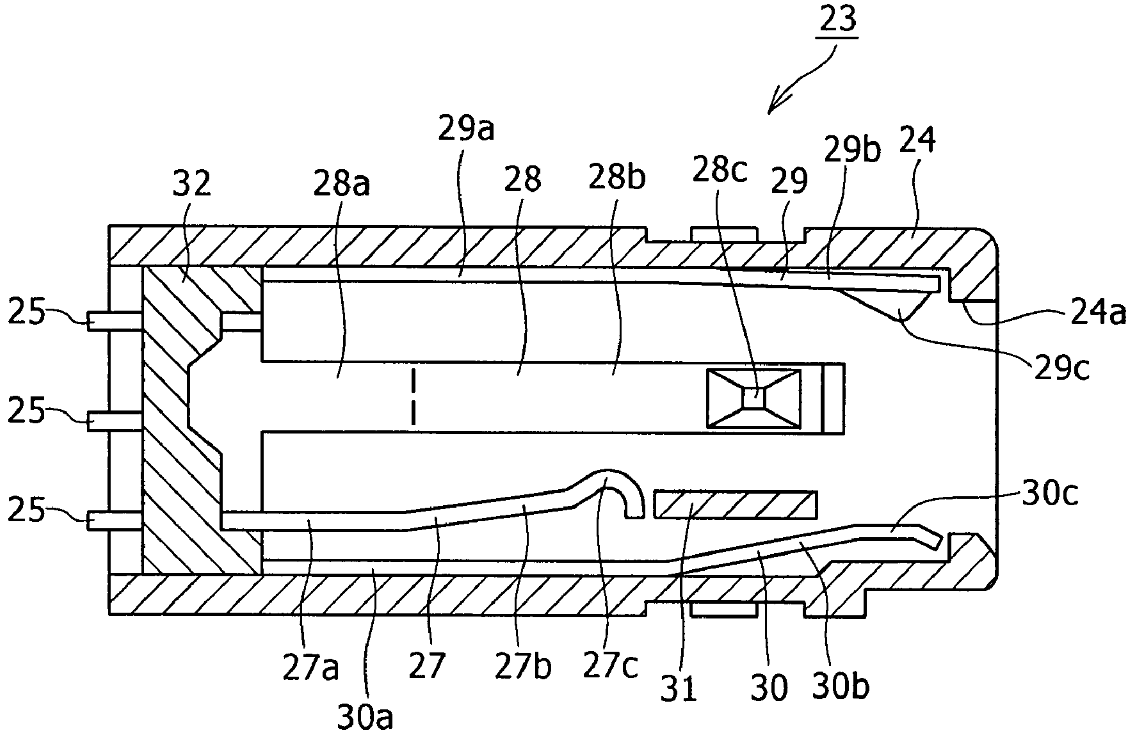
FIG. 10 is a sectional view taken along line X-X of FIG. 8.

Referring to FIGS. 9 and 10, the first, second, third, fourth and fifth connection terminals 26, 27, 28, 29 and 30 are disposed in the inside of the jack 23.

Referring to FIG. 9, the first connection terminal 26 has a base portion 26*a* disposed along the inner face of the jack 23, and a base end portion 26*b* folded back from the base portion 26*a* and extending in a direction away from the plug insertion hole 24*a*. The first connection terminal 26 further has a leaf spring portion 26*c* contiguous to the base end portion 26*b* and bent in a direction away from the base portion 26*a* with respect to the base end portion 26*b*. An end portion of the leaf spring portion 26*c* is formed as a connection portion 26*d*.

Referring to FIG. 10, the second connection terminal 27 has a base end portion 27*a* disposed in parallel to the inner face of the jack 23, and a leaf spring portion 27*b* contiguous to the base end portion 27*a* and bent in a direction away from the inner face of the jack 23 with respect to the base end portion 27*a*. The second connection terminal 27 further has a connection portion 27*c* provided an end portion of the leaf spring portion 27*b* thereof. The connection portion 27*c* is positioned on the plug insertion hole 24*a* side with respect to the connection portion 26*d* of the first connection terminal 26.

Referring to FIG. 9, the third connection terminal 28 has a base end portion 28*a* disposed along the inner face of the jack 23 and a leaf spring portion 28*b* contiguous to the base end portion 28*a* and curved in a direction away from the inner face of the jack 23 with respect to the base end portion 28*a*. A connection portion 28*c* is provided at an end portion of the leaf spring portion 28*b*. The connection portion 28*c* is positioned on the plug insertion hole 24*a* side with respect to the connection portion 27*c* of the second connection terminal 27.

Referring to FIGS. 9 and 10, the fourth connection terminal 29 has a base end portion 29*a* disposed along the inner face of the jack 23, and a leaf spring portion 29*b* contiguous to the base end portion 29*a* and bent in a direction away from the inner face of the jack 23 with respect to the base end portion 29*a*. A connection portion 29*c* is provided at an end portion of the leaf spring portion 29*b*. The connection portion 29*c* is positioned adjacent the plug insertion hole 24*a* with respect to the connection portion 28*c* of the third connection terminal 28 and just on the inner side of the opening of the plug insertion hole 24*a*.

Referring to FIG. 10, the fifth connection terminal 30 has a base end portion 30*a* disposed along the inner side of the jack 23, and a leaf spring portion 30*b* contiguous to the base end portion 30*a* and bent in a direction away from the inner face of the jack 23 with respect to the base end portion 30*a*. A connection portion 30*c* is provided at an end portion of the leaf spring portion 30*b*. The connection portion 30*c* is positioned just on the inner side of the opening of the plug insertion hole 24*a*.

A stopper wall 31 is provided inside the jack 23. The stopper wall 31 is positioned remotely from the inner face of the jack 23 with respect to the leaf spring portion 30*b* of the fifth connection terminal 30.

Referring to FIGS. 9 and 10, a retaining insulating member 32 is provided inside the jack 23. The retaining insulating member 32 is provided at an end portion of the plug insertion hole 24*a* remote from the opening.

The first, second third fourth and fifth connection terminals 26, 27, 28, 29 and 30 are retained with a portion thereof embedded in the retaining insulating member 32 and are individually connected to the terminal pieces 25. Accordingly, the first, second third fourth and fifth connection terminals 26, 27, 28, 29 and 30 are connected to the control circuit provided in the external apparatus 22 through the respective terminal pieces 25.

Figure 11:
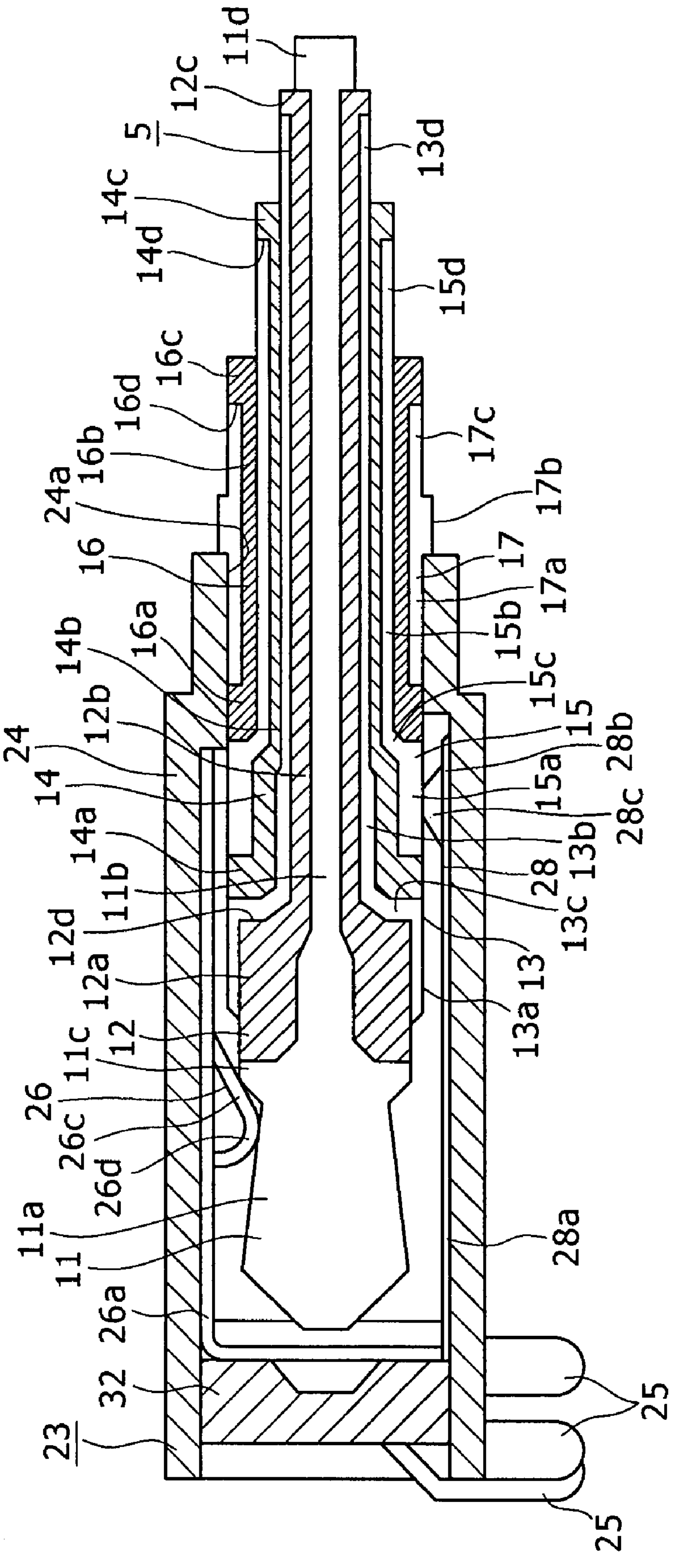
FIG. 11 is an enlarged sectional view of the plug in a state wherein it is connected to the jack.
Figure 12:
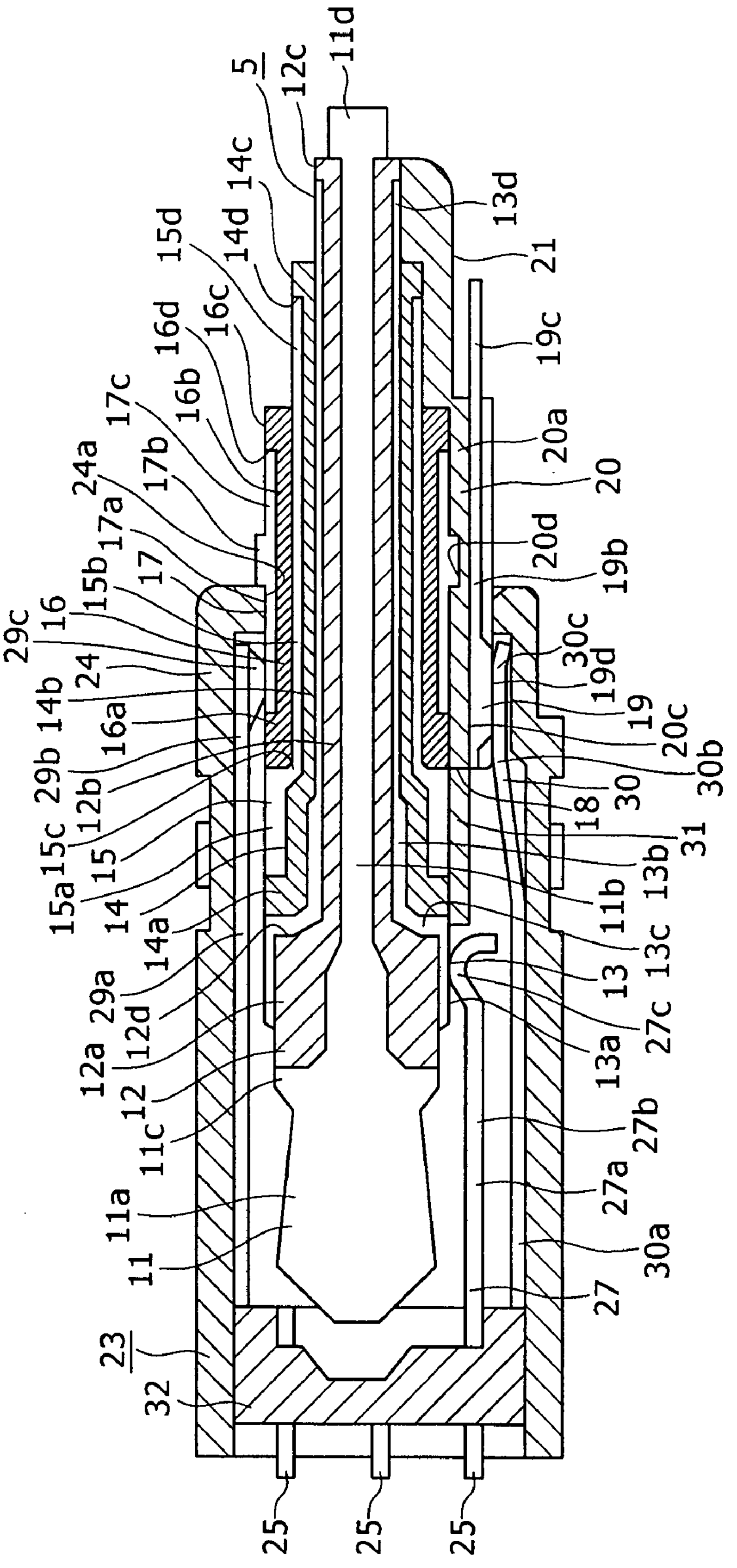
FIG. 12 is an enlarged sectional view showing the plug in the state wherein it is connected to the jack as viewed from a direction different from that in FIG. 11.

Referring to FIGS. 11 and 12, when the plug 5 is inserted in the plug insertion hole 24*a*, the electrode portion 11*a* of the first conductor 11, electrode portion 13*a* of the second conductor 13, electrode portion 15*a* of the third conductor 15, electrode portion 17*a* of the fourth conductor 17 and connection projection 19*d* of the fifth conductor 19 are connected to the connection portion 26*d* of the first connection terminal 26 for the first speaker 7, connection portion 27*c* of the second connection terminal 27 for the second speaker 9, connection portion 28*c* of the third connection terminal 28 for the first microphone 6, connection portion 29*c* of the fourth connection terminal 29 for grounding, and connection portion 30*c* of the fifth connection terminal 30 for the second microphone 8, respectively.

At this time, the plug 5 is inserted to a position at which the projection 17*b* of the fourth conductor 17 contacts with the outer side opening edge of the plug insertion hole 24*a* of the jack 23 and one end face of the insertion portion 19*b* of the fifth conductor 19 contacts with the stopper wall 31. Thus, the plug 5 is positioned with respect to the jack 23 in the insertion direction.

The connection portions 26*d*, 27*c*, 28*c*, 29*c* and 30*c* are resiliently deformed against the spring force with respect to the base end portions 26*b*, 27*a*, 28*a*, 29*a* and base end portion 30*a*, respectively, and are connected in a state wherein they are pressed against the electrode portion 11*a*, electrode portion 13*a*, electrode portion 15*a*, electrode portion 17*a* and connection projection 19*d*.

Figure 13:
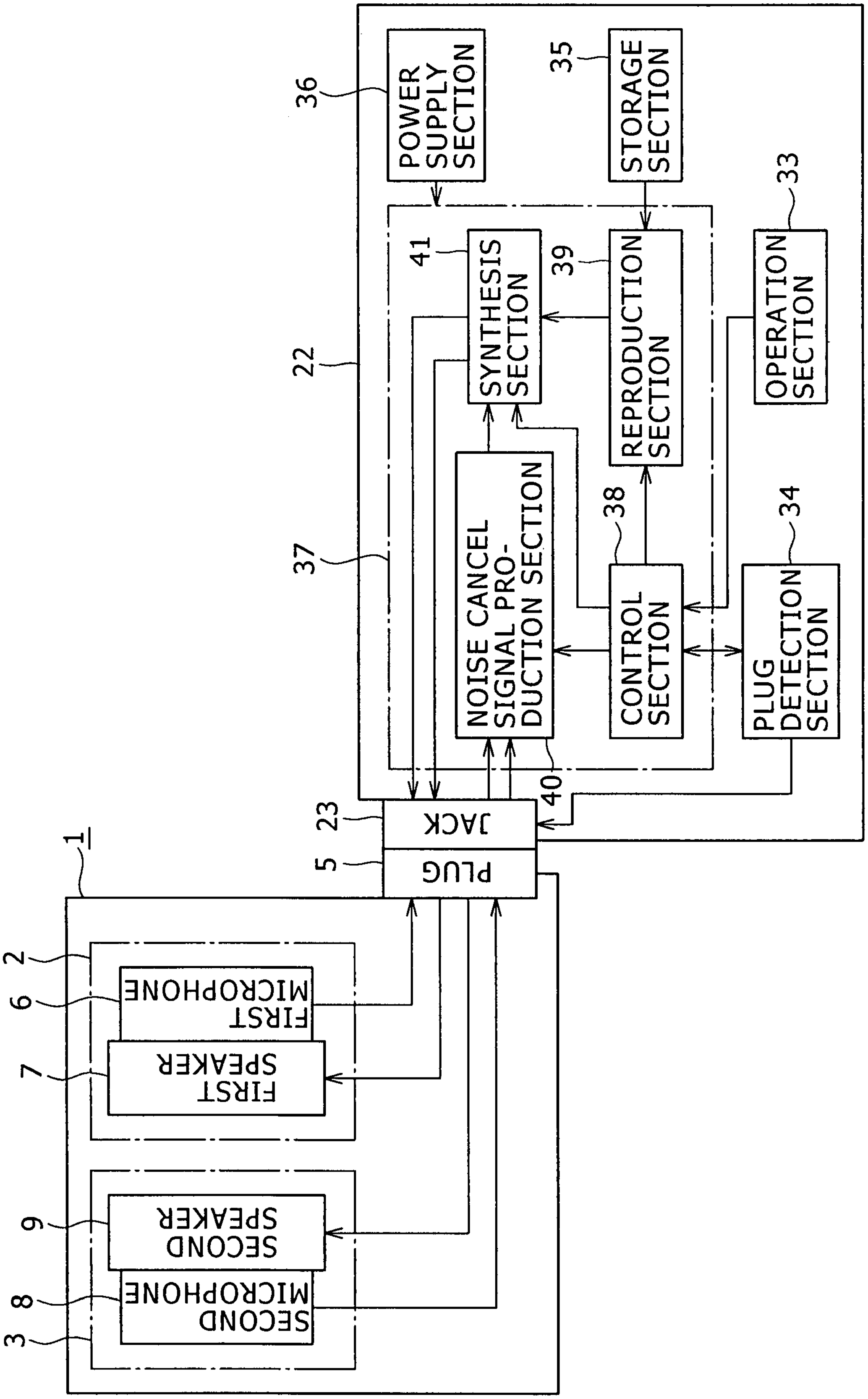
FIG. 13 is a block diagram showing an internal configuration of the sound inputting and outputting apparatus and the external apparatus.

Referring to FIG. 13, the external apparatus 22 includes an operation section 33, a plug detection section 34, a storage section 35 and a power supply section 36.

The operation section 33 includes operation buttons, operation switches and like members for executing various functions such as variation of the sound volume, variation of the sound quality, selection of sound to be reproduced such as selection of a musical piece and so forth.

The plug detection section 34 has a function of detecting a type of a plug inserted in and connected to the jack 23. The plug in this instance may be the plug 5 of the five-pole type having the configuration described hereinabove or a plug of a three-pole configuration, and the plug detection section 34 detects which one of the types the type of the plug connected to the jack 23 is.

The storage section 35 is, for example, a flash memory and stores not only sound signals but also programs and so forth required by the external apparatus 22.

The power supply section 36 typically is a battery and supplies necessary power to the components of the external apparatus 22.

The external apparatus 22 includes a control circuit 37 and operates with power supplied thereto from the power supply section 36. The control circuit 37 includes a control section 38, a reproduction section 39, a noise cancel signal production section 40 and a synthesis section 41.

The control section 38 controls the entire external apparatus 22. For example, the control section 38 signals an instruction signal for canceling noise to the noise cancel signal production section 40 based on a result of detection of the plug detection section 34. Further, the control section 38 signals various instruction signals to the components of the external apparatus 22 such as the reproduction section 39 in response to an operation received from the operation section 33.

The reproduction section 39 reproduces sound data stored in the storage section 35 in response to an instruction signal received from the control section 38 and outputs the reproduced sound data to the synthesis section 41. Thus, the synthesis section 41 produces and outputs first and second sound signals to the first and second speakers 7 and 9, respectively The noise cancel signal production section 40 produces, in response to an instruction signal received from the control section 38, first and second noise cancel signals for first and second noise signals inputted thereto from the control section 38 through the plug 5 and the jack 23. The noise cancel signal production section 40 signals the thus produced noise cancel signals to the synthesis section 41.

The synthesis section 41 synthesizes, in response to an instruction signal received from the control section 38, first and second sound signals inputted thereto from the reproduction section 39 and first and second noise cancel signals inputted thereto from the noise cancel signal production section 40 to produce first and second synthesis signals, respectively. Then, the noise cancel signal production section 40 signals the first synthesis signal to the first speaker 7 of the sound inputting and outputting apparatus 1 through the jack 23 and the plug 5 and signals the second synthesis signal to the second speaker 9 of the sound inputting and outputting apparatus 1 through the jack 23 and the plug 5.

The external apparatus 22 has a display section 22*a* provided thereon as seen in FIG. 1. Referring to FIG. 1, the display section 22*a* displays not only various functions carried out in response to an operation for the operation section 33 and a current execution state of a function but also the type of a plug connected to the jack 23 and so forth. Further, the display section 22*a* displays information regarding the noise cancel function, which is hereinafter described, such as, for example, information that the noise cancel function is executed in a state wherein the plug 5 is connected to the jack 23.

Referring back to FIG. 13, if noise such as external noise is inputted to the first and second microphones 6 and 8 of the external apparatus 22, then noise signals based on the noise are inputted from the first and second microphones 6 and 8 to the noise cancel signal production section 40 through the connection cable 4, plug 5 and jack 23.

When the noise signals are inputted to the noise cancel signal production section 40, the control section 38 operates based on a result of detection, that is, based on a detection signal, signaled from the plug detection section 34 to the control section 38.

At this time, if a detection signal that the plug 5 of the five-pole type is connected to the jack 23 is signaled from the plug detection section 34, then the control section 38 controls the noise cancel signal production section 40 to produce a noise cancel signal.

On the other hand, if another detection signal that a plug of the three-pole type is connected to the jack 23 is signaled from the plug detection section 34, then the control section 38 controls the noise cancel signal production section 40 so as not to execute a noise cancel signal process. Accordingly, where a plug of the three-pole configuration is connected to the jack 23, no noise cancel signal is produced.

Figure 14:
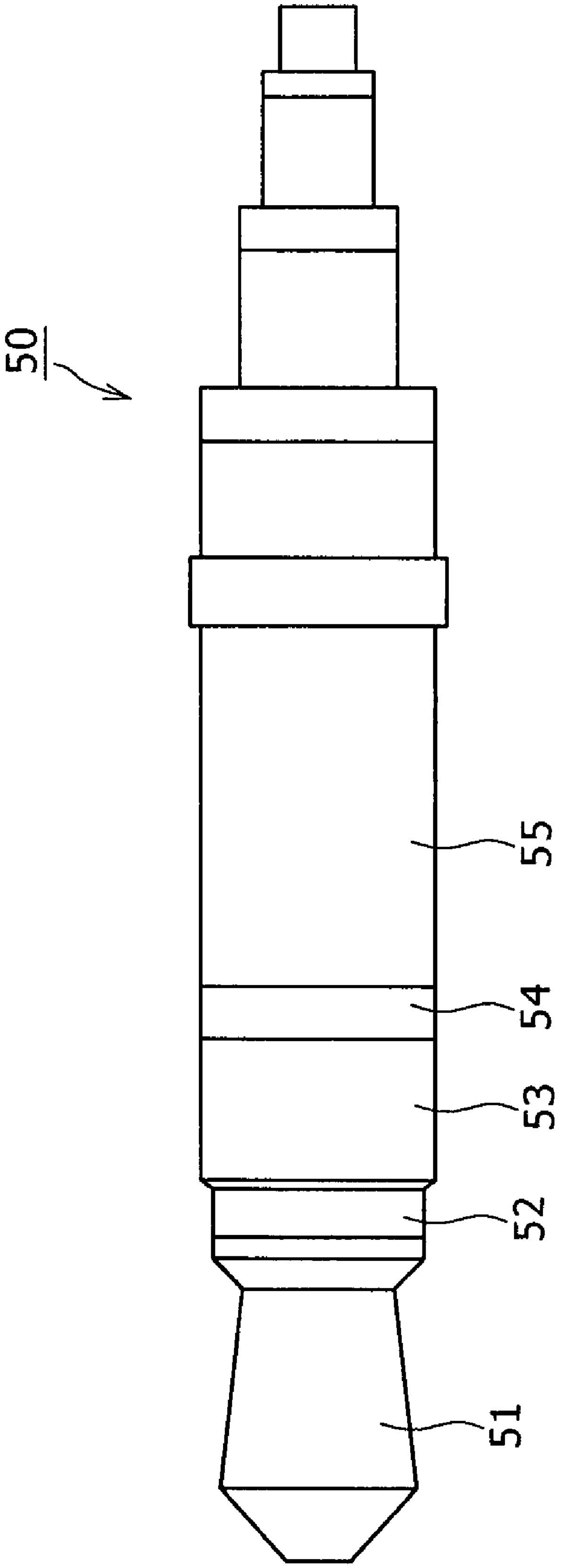
FIG. 14 is an enlarged side elevational view showing a plug having a three-pole configuration.
Figure 15:
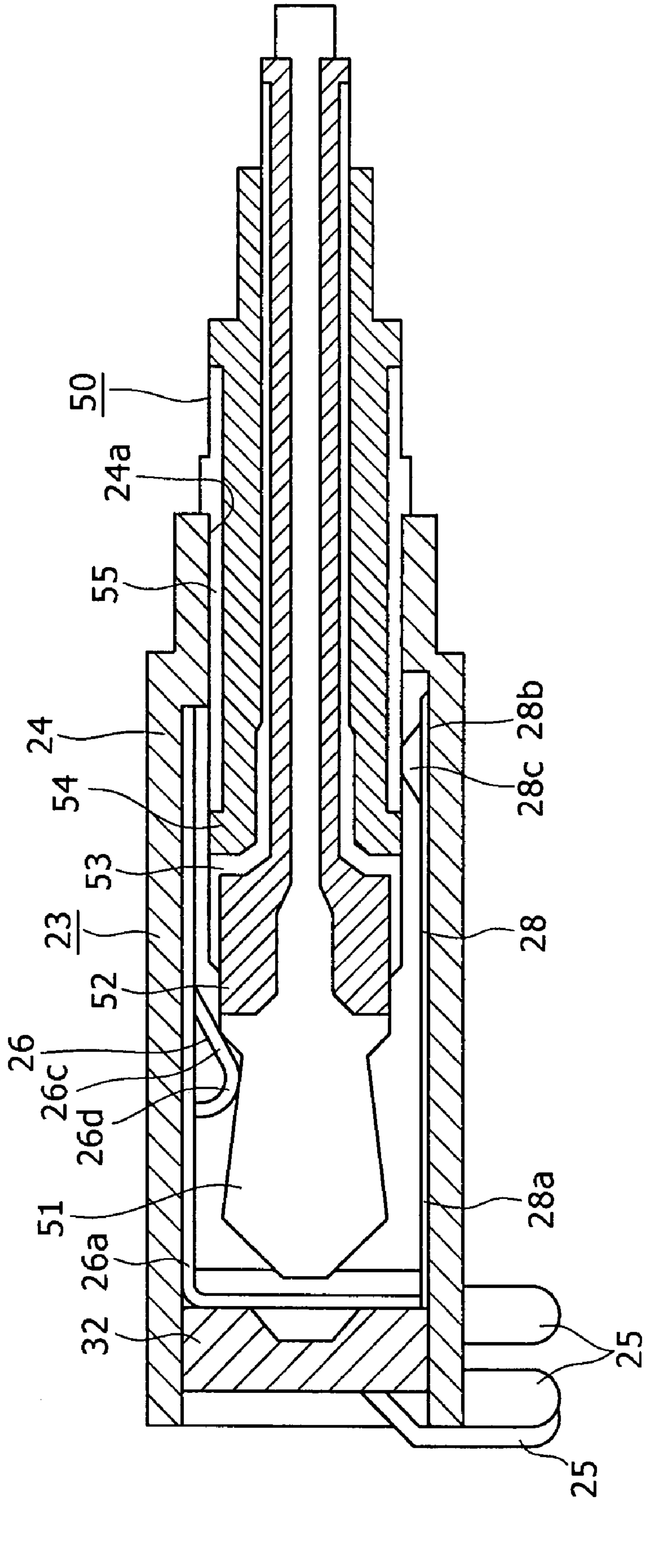
FIG. 15 is an enlarged sectional view showing the plug of a three-pole configuration in a state wherein it is connected to the jack.
Figure 16:
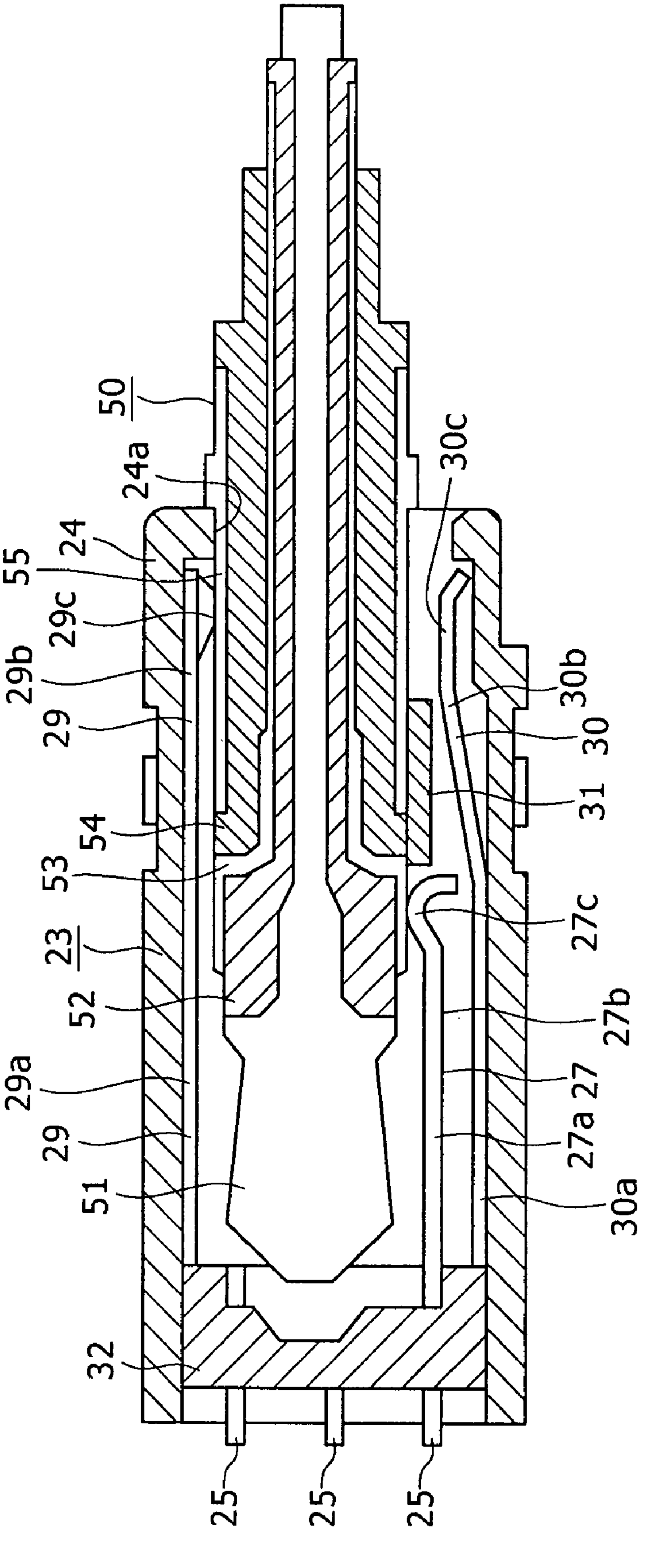
FIG. 16 is an enlarged sectional view showing the plug of a three-pole configuration wherein it is connected to the jack as viewed from a direction different from that in FIG. 15.

Referring now to FIGS. 14 to 16, there is shown a plug 50 of the three-pole type. The plug 50 of the three-pole type shown includes a first conductor 51, a first insulator 52 outwardly fitted on the first conductor 51, a second conductor 53 outwardly fitted on the first insulator 52, a second insulator 54 outwardly fitted on the second conductor 53 and a third conductor 55 outwardly fitted on the second insulator 54. In a state wherein the plug 50 is connected to the jack 23, the first conductor 51 is connected to the first connection terminal 26 for the first speaker 7 and the second conductor 53 is connected to the second connection terminal 27 for the second speaker 9 while the third conductor 55 is connected to the fourth connection terminal 29 for grounding. The plug 50 is not connected to the fifth connection terminal 30 for the second microphone 8.

While the plug 50 is configured such that the third conductor 55 thereof contacts also with the third connection terminal 28 for the first microphone 6, the control circuit 37 of the external apparatus 22 is configured such that no signal is communicated between the third conductor 55 and the third connection terminal 28. It is to be noted that, for example, the arrangement position of the third connection terminal 28 of the jack 23 may be changed so that, when the plug 50 is connected to the jack 23, the third conductor 55 is not connected to the third connection terminal 28.

Figure 17:
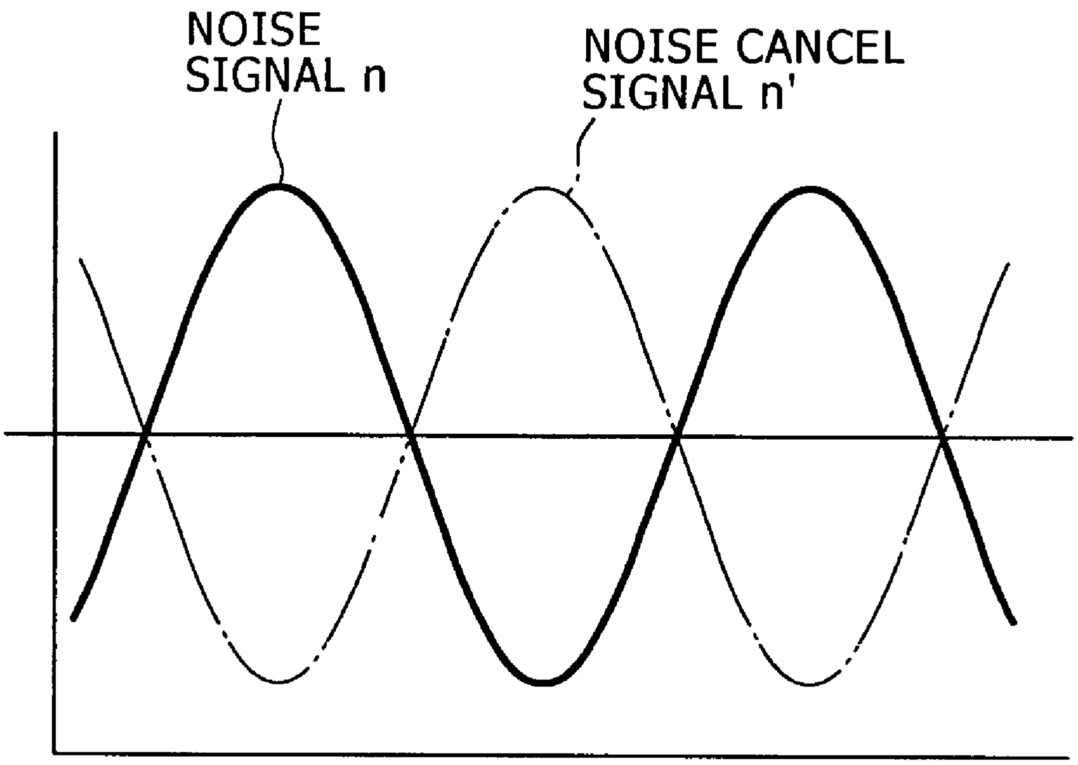
FIG. 17 is a graph illustrating a noise signal and a noise cancel signal.

If an instruction signal to produce a noise cancel signal is signaled from the control section 38 to the noise cancel signal production section 40 as described hereinabove, then a noise cancel signal n' which has a phase opposite to that of a noise signal n as seen in FIG. 17 is produced by the noise cancel signal production section 40.

After the noise cancel signal is produced by the noise cancel signal production section 40, it is signaled to the synthesis section 41. Simultaneously, a sound signal is signaled from the reproduction section 39 to the synthesis section 41. Consequently, the synthesis section 41 produces a synthesis signal wherein the noise cancel signal and the sound signal are synthesized.

The thus produced synthesis signal (first and second synthesis signals) is signaled from the synthesis section 41 to the first and second speakers 7 and 9 of the sound inputting and outputting apparatus 1 through the jack 23, plug 5 and connection cable 4.

After the synthesis signal is signaled to the first and second speakers 7 and 9, the sound signal is inputted to the auricles 100 and 200 of the user in a state wherein the noise inputted from the outside is cancelled by the noise cancel signal.

As described above, in the sound inputting and outputting apparatus 1, the plug 5 has a five-pole configuration and noise cancellation is performed by the control circuit 37 of the external apparatus 22. Consequently, miniaturization of the sound inputting and outputting apparatus 1 is assured and execution of the noise cancel function can be assured simultaneously.

Further, since, in the plug 5, the five-pole configuration is achieved by attaching an electrode to an outer circumferential face of a four-pole configuration portion having a shape of a substantially round bar, the plug 5 of the five-pole configuration can be formed readily.

Furthermore, since, in the plug 5, the fifth conductor 19 is formed like a plate and attached at one face thereof in a thicknesswise direction to the fourth insulator 18, the overall outer diameter of the plug 5 can be reduced. Consequently, miniaturization can be anticipated.

Further, since the connecting projection **19*d* which functions as an electrode element is provided on the fifth conductor 19, good connection performance can be assured between the fifth conductor 19 and the fifth connection terminal 30 of the jack 23**.

Further, since, in the plug 5, the fourth insulator 18 and the fifth conductor 19 are attached to the four-pole configuration portion formed as a substantially round bar, the fourth insulator 18 and the fifth conductor 19 are so shaped as to project forwardly from the substantially round bar portion. Consequently, insertion in error into a jack for exclusive use with a plug of the three-pole configuration wherein the plug insertion hole is formed in a circular shape can be prevented.

In the sound inputting and outputting apparatus 1, since the first and second microphones 6 and 8 are disposed on the outer side with respect to the first and second speakers 7 and 9, respectively, the first and second microphones 6 and 8 are positioned remotely from the drum membrane of the user with respect to the first and second speakers 7 and 9, respectively. Consequently, execution of noise cancellation can be carried out by feedforward type control.

Further, in the external apparatus 22, the plug detection section 34 for detecting the connection state of a plug to the jack 23 is provided such that the noise cancel function is executed when the plug 5 of the five-pole configuration is connected to the jack 23. Consequently, when the plug 50 of the three-pole configuration is connected to the jack 23, the noise cancel function is not executed. Consequently, simplification of control by prevention of execution of an unnecessary function can be achieved.

Further, in the external apparatus 22, when it is detected by the plug detection section 34 that the plug 5 is connected to the jack 23, the information that the noise cancel function is executed is displayed on the display section **22*a* of the external apparatus 22**. Consequently, the user can confirm that the noise cancel function is executed, and accordingly, improvement in convenience in use can be anticipated.

It is to be noted that a display section may be provided on the sound inputting and outputting apparatus 1. In this instance, when it is detected by the plug detection section 34 that the plug 5 is connected to the jack 23, the information that the noise cancel function is executed or can be executed is displayed on the display section of the sound inputting and outputting apparatus 1.

Further, the control section 38, reproduction section 39, noise cancel signal production section 40 and synthesis section 41 described hereinabove with reference to FIG. 13 may be formed by software or by hardware.

While a preferred embodiment of the present invention has been described using specific terms, such description is for illustrative purposes only, and it is to be understood that changes and variations may be made without departing from the spirit or scope of the following claims.

The invention claimed is:

1. A sound inputting and outputting apparatus for being connected to an external apparatus which includes a noise cancel signal production section for producing, in response to a noise signal inputted thereto, a noise cancel signal for reducing the noise signal, a storage section and a reproduction section for reproducing sound data stored in the storage section, the sound inputting and outputting apparatus comprising:

a first auricle mounting section including a first microphone and a first speaker;

a second auricle mounting section including a second microphone and a second speaker; and a plug including a first conductor configured to output a first noise signal to the external apparatus in response to first noise inputted to said first microphone, a second conductor configured to output a second noise signal to the external apparatus in response to second noise inputted to said second microphone, a third conductor configured to transmit a first synthesis signal of a first noise cancel signal produced by the noise cancel signal production section in response to the first noise signal and a first sound signal reproduced by the reproduction section to said first speaker, a fourth conductor for grounding, and a fifth conductor configured to transmit a second synthesis signal of a second noise cancel signal produced by the noise cancel signal production section in response to the second noise signal and a second sound signal reproduced by the reproduction section to said second speaker, said plug being configured to be inserted into a jack provided on the external apparatus to establish connection thereof to the external apparatus.

2. The sound inputting and outputting apparatus according to claim 1, wherein said first and second microphones are disposed remotely from a sound outputting side of said first and second speakers with respect to said first and second speakers, respectively.

3. The sound inputting and outputting apparatus according to claim 1, wherein said first conductor includes a first electrode portion and a first fitting portion and is formed like a round bar;

said second conductor includes a second electrode portion and a second fitting portion;

said third conductor includes a third electrode portion and a third fitting portion;

said fourth conductor includes a fourth electrode portion;

said plug further includes:

a first insulator outwardly fitted on said first fitting portion of said first conductor to isolate said first and second conductors from each other;

a second insulator outwardly fitted on said second fitting portion of said second conductor to isolate said second and third conductors from each other;

a third insulator outwardly fitted on said third fitting portion of said third conductor to isolate said third and fourth conductors from each other; and a fourth insulator attached to at least part of an outer face of said fourth conductor; and said fifth conductor is attached to but isolated from said fourth insulator.

4. The sound inputting and outputting apparatus according to claim 3, wherein said fourth insulator has a conductor attachment groove having said fifth conductor fitted therein to hold said fifth conductor, and said fifth conductor has an insertion portion inserted in said conductor attachment groove.

5. The sound inputting and outputting apparatus according to claim 4, wherein said fifth conductor has a connecting projection provided at one end of said insertion portion thereof for being connected to the jack.

6. The sound inputting and outputting apparatus according to claim 5, wherein said fifth conductor has a blocking projection configured to engage with one end face of said fourth insulator to block said insertion portion against insertion into said conductor attachment groove.

7. The sound inputting and outputting apparatus according to claim 6, wherein said fifth conductor includes a cable connection portion at an end thereof remote from said insertion portion with respect to said blocking projection.

8. The sound inputting and outputting apparatus according to claim 3, wherein each of said first, second and third conductors is formed such that said fitting portion thereof has a diameter smaller than that of the electrode portion thereof while each of said first, second and third insulators has a large diameter portion which is exposed at least part thereof to an outer face thereof and a small diameter portion having a diameter smaller than that of said large diameter portion, and each of the fitting portions of said second and third conductors and said fourth conductor is outwardly fitted on said smaller diameter portion of said first, second or third insulator.

9. The sound inputting and outputting apparatus according to claim 8, wherein said fourth insulator is formed so as to engage with said large diameter portion of said third insulator.

10. The sound inputting and outputting apparatus according to claim 9, wherein each of said first, second, third and fourth conductors has a cable connection portion remote from said electrode portion thereof while each of said first, second and third insulators has an outwardly swollen portion remote from said large diameter portion, and said fourth insulator has an extension configured to engage with said outwardly swollen portion of said first insulator.

11. The sound inputting and outputting apparatus according to claim 7, wherein said fourth conductor has a projection provided in a projecting manner in a radial direction of the round bar between said electrode portion and said cable connection portion thereof while said fourth insulator has a fitting groove configured to fit with said projection.

12. The sound inputting and outputting apparatus according to claim 11, further comprising a cover configured to close up the cable connection portions of said first, second, third and fourth conductors.

13. A sound signal processing apparatus, comprising:

a noise cancel signal production section configured to produce first and second noise cancel signals in response to first and second noise signals outputted from first and second microphones of a sound inputting and outputting apparatus in response to first noise and second noise inputted to the first and second microphones, respectively;

a reproduction section configured to reproduce sound data stored in a storage section and output first and second sound signals;

a synthesis section configured to synthesize the first and second noise cancel signals with the first and second sound signals to produce first and second synthesis signals, respectively; and a jack configured to be fitted with a plug of a five-pole configuration provided on the sound inputting and outputting apparatus and including a first conductor configured to transmit the first noise signal outputted from the first microphone, a second conductor configured to transmit the second noise signal outputted from the second microphone, a third conductor configured to transmit the first synthesis signal to the first speaker of the sound inputting and outputting apparatus, a fourth conductor for grounding, and a fifth conductor configured to transmit the second synthesis signal to the second speaker of the sound inputting and outputting apparatus.

14. The sound signal processing apparatus according to claim 13, further comprising:

a detection section configured to detect whether the plug of the five-pole configuration is inserted in said jack; and a control section configured to control said noise cancel signal production section to execute the noise cancel signal production process in response to a result of the detection by said detection section.

15. The sound signal processing apparatus according to claim 14, further comprising a display section to be controlled by said control section to display information regarding the noise cancel function, if the plug of the five-pole configuration is inserted in said jack, in response to the result of the detection by said detection section.

16. A noise cancel system, comprising:

a sound signal processing apparatus; and a sound signal inputting and outputting apparatus;

said sound signal processing apparatus including:

a noise cancel signal production section configured to produce a noise cancel signal in response to a noise signal inputted thereto;

a reproduction section configured to reproduce a sound signal stored in a storage section; and a jack;

said sound signal inputting and outputting apparatus including:

a first auricle mounting section including a first microphone and a first speaker;

a second auricle mounting section including a second microphone and a second speaker; and a plug of a five-pole configuration including a first conductor configured to output a first noise signal to said sound signal processing apparatus in response to first noise inputted to said first microphone, a second conductor configured to output a second noise signal to said sound signal processing apparatus in response to second noise inputted to said second microphone, a third conductor configured to transmit a first synthesis signal of a first noise cancel signal produced by said noise cancel signal production section in response to the first noise signal and a first sound signal reproduced by said reproduction section to said first speaker, a fourth conductor for grounding, and a fifth conductor configured to transmit a second synthesis signal of a second noise cancel signal produced by said noise cancel signal production section in response to the second noise signal and a second sound signal reproduced by said reproduction section to said second speaker, said plug being configured to be inserted into a jack provided of said sound signal processing apparatus to establish connection between said sound inputting apparatus and said sound signal processing apparatus.

17. The noise cancel system according to claim 16, wherein said sound signal processing apparatus further includes:

a detection section configured to detect whether said plug of the five-pole configuration is inserted in said jack; and a control section configured to control said noise cancel signal production section to produce the noise cancel signal in response to a result of the detection by said detection section.

18. The noise cancel system according to claim 16, wherein said sound signal processing apparatus further includes a display section to be controlled by said control section to display information regarding a noise cancel function if said plug of the five-pole configuration is inserted in said jack in response to the result of the detection by said detection section.

19. The noise cancel system according to claim 16, wherein said first and second microphones are disposed remotely from a sound outputting side of said first and second speakers with respect to said first and second speakers, respectively.

20. A plug for being inserted in a jack of an external apparatus which includes a noise cancel signal production section and a reproduction section to establish connection of first and second microphones and first and second speakers provided in a sound inputting and outputting apparatus to the external apparatus, the plug comprising:

a first conductor configured to transmit a first noise signal to the external apparatus in response to first noise inputted to the first microphone;

a second conductor configured to transmit a second noise signal to the external apparatus in response to second noise inputted to the second microphone;

a third conductor configured to transmit a first synthesis signal of a first noise cancel signal produced by the noise cancel signal production section in response to the first noise signal and a first sound signal reproduced by the reproduction section to the first speaker;

a fourth conductor for grounding; and a fifth conductor configured to transmit a second synthesis signal of a second noise cancel signal produced by the noise cancel signal production section in response to the second noise signal and a second sound signal reproduced by the reproduction section to the second speaker.

21. The plug according to claim 20, wherein said first conductor includes a first electrode portion and a first fitting portion and is formed like a round bar;

said second conductor includes a second electrode portion and a second fitting portion;

said third conductor includes a third electrode portion and a third fitting portion;

said fourth conductor includes a fourth electrode portion;

said plug further includes:

a first insulator outwardly fitted on said first fitting portion of said first conductor to isolate said first and second conductors from each other;

a second insulator outwardly fitted on said second fitting portion of said second conductor to isolate said second and third conductors from each other;

a third insulator outwardly fitted on said third fitting portion of said third conductor to isolate said third and fourth conductors from each other; and a fourth insulator attached to at least part of an outer face of said fourth conductor; and said fifth conductor is attached to but isolated from said fourth insulator.

22. The plug according to claim 21, wherein said fourth insulator has a conductor attachment groove having said fifth conductor fitted therein to hold said fifth conductor, and said fifth conductor has an insertion portion inserted in said conductor attachment groove.

23. The plug according to claim 22, wherein said fifth conductor has a connecting projection provided at one end of said insertion portion thereof for being connected to said jack.

24. The plug according to claim 23, wherein said fifth conductor has a blocking projection configured to engage with one end face of said fourth insulator to block said insertion portion against insertion into said conductor attachment groove.

25. The plug according to claim 24, wherein said fifth conductor includes a cable connection portion at an end thereof remote from said insertion portion with respect to said blocking projection.

26. The plug according to claim 25, wherein each of said first, second and third conductors is formed such that said fitting portion thereof has a diameter smaller than that of the electrode portion thereof while each of said first, second and third insulators has a large diameter portion which is exposed at least part thereof to an outer face thereof and a small diameter portion having a diameter smaller than that of said large diameter portion, and each of the fitting portions of said second and third conductors and said fourth conductor is outwardly fitted on said smaller diameter portion of said first, second or third insulator.

27. The plug according to claim 25, wherein said fourth insulator is formed so as to engage with said large diameter portion of said third insulator.

28. The plug according to claim 27, wherein each of said first, second, third and fourth conductors has a cable connection portion remote from said electrode portion thereof while each of said first, second and third insulators has an outwardly swollen portion remote from said large diameter portion, and said fourth insulator has an extension configured to engage with said outwardly swollen portion of said first insulator.

29. The plug according to claim 28, wherein said fourth conductor has a projection provided in a projecting manner in a radial direction of the round bar between said electrode portion and said cable connection portion thereof while said fourth insulator has a fitting groove configured to fit with said projection.

30. The plug according to claim 29, further comprising a cover configured to close up the cable connection portions of said first, second, third and fourth conductors.

* * * * *